(12) United States Patent
Fleckenstein et al.

(10) Patent No.: US 7,968,696 B1
(45) Date of Patent: Jun. 28, 2011

(54) VIRAL INTERLEUKIN-6

(75) Inventors: Bernhard Fleckenstein, Wiesenthau (DE); Jens-Christian Albrecht, Fuerth (DE); Frank Neipel, Uttenreuth (DE); Alvin Friedman-Kien, New York, NY (US); Yao-Qi Huang, New York, NY (US)

(73) Assignees: Behring Diagnostics GmbH, Marburg (DE); New York University, New York, NY (US)

( * ) Notice: Subject to any disclaimer, the term of this patent is extended or adjusted under 35 U.S.C. 154(b) by 2783 days.

(21) Appl. No.: 09/230,048

(22) PCT Filed: Jul. 19, 1996

(86) PCT No.: PCT/EP96/03199
§ 371 (c)(1),
(2), (4) Date: Mar. 12, 1999

(87) PCT Pub. No.: WO98/03657
PCT Pub. Date: Jan. 29, 1998

(51) Int. Cl.
*C07H 21/04* (2006.01)
*C07K 14/00* (2006.01)
*C12P 21/06* (2006.01)
*C12N 5/00* (2006.01)
*C12N 15/00* (2006.01)

(52) U.S. Cl. .............. 536/23.72; 536/23.1; 536/23.5; 530/350; 530/351; 435/69.1; 435/320.1; 435/325; 435/455

(58) Field of Classification Search ............ 435/69.1, 435/328, 386, 406, 455; 514/2, 44; 530/351; 536/23.1, 23.5, 23.7, 23.72
See application file for complete search history.

(56) References Cited

U.S. PATENT DOCUMENTS

| 5,200,313 A | * | 4/1993 | Carrico ............... 435/6 |
| 5,831,064 A | * | 11/1998 | Chang et al. ........... 536/23.72 |
| 5,861,240 A | * | 1/1999 | Ganem et al. .......... 435/5 |

FOREIGN PATENT DOCUMENTS

WO  8800206  *  1/1988

OTHER PUBLICATIONS

Verma et al., Nature, 389:239-242, 1997.*
Mullberg et al., J. Immunol., 164:4672-4677, 2000.*
Hoischen at al., Eur. J. Biochem., 267:3604-3612, 2000.*
Molden at al., J. Biol. Chem., 272:19625-19631, 1997.*
Wan et al., J. Virology, 73:8268-8278, 1999.*
Chang et al., Science, 266:1865-1869, 1994.*
H.R. Maurer, in Animal Cell Culture—A Practical Approach, ed. R.I. Freshney, IRL Press Limited, Oxford, England, pp. 13-31, 1987.*
Orkin et al. in "Report and Recommendations of the Panel to Assess the NIH Investment in Research on Gene Therapy", Dec. 1995.*
Neipel, F., et al., "Human Herpesvirus 8 Encodes a Homolog of Interleukin-6," Journal of Virology, vol. 71, No. 1, pp. 839-842 (1997).
Russo, J., et al., "Nucleotide Sequence of the Kaposi Sarcoma-Associated Herpesvirus (HHV8)," Proc. Natl. Acad. Sci. USA, vol. 93, pp. 14862-14867 (1996).
Moore, P., et al., "Molecular Mimicry of Human Cytokine and Cytokine Response Pathway Genes by KSHV," Science, vol. 274, pp. 1739-1744 (1996).
Zhong, W., et al., "Restricted Expression of Kaposi Sarcoma-Associated Herpesvirus (Human Herpesvirus 8) Genes in Kaposi Sarcoma," Proc. Natl. Acad. Sci. USA, vol. 93, pp. 6641-6646, (1996).

* cited by examiner

*Primary Examiner* — Sumesh Kaushal
(74) *Attorney, Agent, or Firm* — Klauber & Jackson LLC

(57) ABSTRACT

The present invention relates to viral interleukin-6 (v-IL-6), which can be obtained by recombinant expression of the DNA of human herpesvirus type 8 (HHV-8), and which may be used in diagnosis and treatment of human diseases such as kaposi sarcoma, Castleman's disease, multiple myeloma, kidney cell carcinoma, mesangial proliferative glomerulonephritis or B cell lymphoma.

6 Claims, 4 Drawing Sheets

Fig. 1:

```
              1                                                         56
Il6 human    MnsFStsaFgPVAFsLGLLLVlpaAFPapvppgeDskDvaaPhRQpLTsSErIDkq
Il6 mouse    MkFLSaRdFhPVAF.LGLMLVttTAFPtsqvrRGDFtEdttPnRpVyTtSQ.VGgl
Il6 hhv8     McWFklWsL....LlVGsLLVsgT........RGkLpDapefeKDLLi......qr
Consensus    *                *   **

57                                                        112
Il6 human    IrYILdgIsaLRKEtCNKsnMCeSskEALAENNLnLPkMaEkDGCFQsGFNEEtCL
Il6 mouse    IthVLWeIvEMRKELCNgnSdCmnndDALAENNLKLPeIqrnDGCYQtGYNQEiCL
Il6 hhv8     LnWMLWvIdEcfRDLCyRtGICkGilEpaAifhLKLPaInDtDhCgliGFNEtsCL
Consensus        *  *      *     *       *    *  **    * *    * *   **
                           ^      ^                          ^       ^

113                                                       168
Il6 human    VKIitGLLEFEVYLEYLqNrF.EsSeEqARaVQMsTKvLIQFLQkkaKNLdaIttP
Il6 mouse    LKIssGLLEYhsYLEYMkNnLkDnkkDkARVLQrdTeTLIHIFnQEVKDLhKIvlP
Il6 hhv8     kKLadGFFEFEVlFkFLtteF.GkSvinvdVMELlTKTLgwdIQEELnkLtKthys
Consensus      *  *  *                  *    *                  *

169                                                       223
Il6 human    dPttNASLLtKLQAQnQWLqdmTtHLILRSFkEFLqssLRaLRQM..........
Il6 mouse    tPisNAlLtDKLESQKEWLRtkTiQFILKSLEEFLkvtLRstRQt..........
Il6 hhv8     pPkfDrGLLGRLQGlKyWVRhfasfYVLsaMEkFagqaVRvLdsIpdvtpdvhdk
Consensus       *    *    *      *       *      *
```

Fig. 2a

SEQUENCE LISTING

1. Sequence characteristics:
    1.1. Length: 612 base pairs
    1.2. Type: Nucleic Acid
    1.3. Strandedness: Double stranded
    1.4. Topology: Linear
2. Molecule type: Genomic DNA
3. Description: Human herpesvirus 8 interleukin-6 gene
4. Hypothetical: No
5. Anti-sense: No
6. Original source: Kaposi Sarkoma from HIV positive donor
7. Organism: Human herpesvirus 8

Fig. 2b

```
  1  ATG TGC TGG TTC AAG TTG TGG TCT CTC TTG CTG GTC GGT TCA CTG
  1   M   C   W   F   K   L   W   S   L   L   L   V   G   S   L
  1  Met Cys Trp Phe Lys Leu Trp Ser Leu Leu Leu Val Gly Ser Leu

46  CTG GTA TCT GGA ACG CGG GGC AAG TTG CCG GAC GCC CCC GAG TTT
 16   L   V   S   G   T   R   G   K   L   P   D   A   P   E   F
 16  Leu Val Ser Gly Thr Arg Gly Lys Leu Pro Asp Ala Pro Glu Phe

91  GAA AAG GAT CTT CTC ATT CAG AGA CTC AAT TGG ATG CTA TGG GTG
 31   E   K   D   L   L   I   Q   R   L   N   W   M   L   W   V
 31  Glu Lys Asp Leu Leu Ile Gln Arg Leu Asn Trp Met Leu Trp Val

136  ATC GAT GAA TGC TTC CGC GAC CTC TGT TAC CGT ACC GGC ATC TGC
 46   I   D   E   C   F   R   D   L   C   Y   R   T   G   I   C
 46  Ile Asp Glu Cys Phe Arg Asp Leu Cys Tyr Arg Thr Gly Ile Cys

181  AAG GGT ATT CTA GAG CCC GCT GCT ATT TTT CAT CTG AAA CTA CCA
 61   K   G   I   L   E   P   A   A   I   F   H   L   K   L   P
 61  Lys Gly Ile Leu Glu Pro Ala Ala Ile Phe His Leu Lys Leu Pro

226  GCC ATC AAC GAT ACT GAT CAC TGC GGG TTA ATA GGA TTT AAT GAG
 76   A   I   N   D   T   D   H   C   G   L   I   G   F   N   E
 76  Ala Ile Asn Asp Thr Asp His Cys Gly Leu Ile Gly Phe Asn Glu

271  ACT AGC TGC CTT AAA AAG CTC GCC GAT GGC TTT TTT GAA TTC GAG
 91   T   S   C   L   K   K   L   A   D   G   F   F   E   F   E
 91  Thr Ser Cys Leu Lys Lys Leu Ala Asp Gly Phe Phe Glu Phe Glu

316  GTG TTG TTT AAG TTT TTA ACG ACG GAG TTT GGA AAA TCA GTG ATA
106   V   L   F   K   F   L   T   T   E   F   G   K   S   V   I
106  Val Leu Phe Lys Phe Leu Thr Thr Glu Phe Gly Lys Ser Val Ile

361  AAC GTG GAC GTC ATG GAG CTT CTG ACG AAG ACC TTA GGA TGG GAC
121   N   V   D   V   M   E   L   L   T   K   T   L   G   W   D
121  Asn Val Asp Val Met Glu Leu Leu Thr Lys Thr Leu Gly Trp Asp

406  ATA CAG GAA GAG CTC AAT AAG CTG ACT AAG ACG CAC TAC AGT CCA
136   I   Q   E   E   L   N   K   L   T   K   T   H   Y   S   P
136  Ile Gln Glu Glu Leu Asn Lys Leu Thr Lys Thr His Tyr Ser Pro

451  CCC AAA TTT GAC CGC GGT CTA TTA GGG AGG CTT CAG GGA CTT AAG
151   P   K   F   D   R   G   L   L   G   R   L   Q   G   L   K
151  Pro Lys Phe Asp Arg Gly Leu Leu Gly Arg Leu Gln Gly Leu Lys

496  TAT TGG GTG AGA CAC TTT GCT TCG TTT TAT GTT CTG AGT GCA ATG
166   Y   W   V   R   H   F   A   S   F   Y   V   L   S   A   M
166  Tyr Trp Val Arg His Phe Ala Ser Phe Tyr Val Leu Ser Ala Met
```

Fig. 2c

```
541  GAA AAG TTT GCA GGT CAA GCG GTG CGT GTT TTG GAC TCT ATC CCA
181   E   K   F   A   G   Q   A   V   R   V   L   D   S   I   P
181  Glu Lys Phe Ala Gly Gln Ala Val Arg Val Leu Asp Ser Ile Pro

586  GAC GTG ACT CCT GAC GTC CAC GAT AAG
196   D   V   T   P   D   V   H   D   K
196  Asp Val Thr Pro Asp Val His Asp Lys
```

VIRAL INTERLEUKIN-6

CROSS-REFERENCE TO RELATED APPLICATIONS

This is a national stage filing from Priority Application PCT/EP96/03199, filed Jul. 19, 1996.

STATEMENT REGARDING FEDERALLY SPONSORED RESEARCH OR DEVELOPMENT

Not applicable.

BACKGROUND AND SUMMARY OF THE INVENTION

1. Field of the Invention

The invention relates to diagnosis and treatment of diseases such as kaposi sarcoma, Castleman's disease, multiple myeloma, kidney cell carcinoma, mesangial proliferative glomerulonephritis or B cell lymphoma and relates more particularly to viral interleukin 6 for the diagnosis and treatment of human disease.

Kaposi's sarcoma (KS), a multifocal proliferative lesion of uncertain pathogenesis, is highly prevalent among homosexual AIDS patients. Studies with biopsy materials and cultured cells have indicated an important role of growth factors and cellular cytokines, such as basic fibroblast growth factor, interleukin-1β, platelet derived growth factor, interleukin-6 (IL-6), and oncostatin M for the proliferation of spindle cells in KS[1,2]. Several groups found indication for the expression of interleukin-6 (IL-6) receptors in AIDS-KS cells[3] and derived spindle cell lines[4]. As epidemiological evidence had suggested that an infectious agent other than HIV may also be involved in KS pathogenesis, it stirred considerable interest when Chang and colleagues[5] found DNA sequences of a novel herpesvirus in AIDS-KS tissues. Meanwhile, DNA of this virus was consistently found in all epidemiological forms of KS. The new virus, termed human herpesvirus 8 (HHV-8), shows marked sequence homology to herpesvirus (h.) saimiri, the prototype of $_{\gamma 2}$-herpesviruses; thus HHV-8 appears to be the first human member of $_{\gamma 2}$-herpesviruses (genus rhadinovirus). Cloning HHV-8 DNA from KS tissues and sequencing indicates a genome organization that is generally collinear to h. saimiri[6].

BRIEF DESCRIPTION OF THE DRAWINGS

FIG. 1: Alignment of the sequences of the predicted protein precursor (SEQ ID NO: 2) of the HHV-8 IL-6 gene with human (SEQ ID NO: 3) and mouse IL-6 (SEQ ID NO: 4). Amino acids identical in all three proteins are indicated by an asterisk, cysteine residues involved in disulfide bridging are marked with an arrowhead. Upper case letters symbolize amino acids conserved according to Dayhoff criteria.

FIG. 2: Nucleic acid sequence encoding v-IL-6 (SEQ ID NO: 1) and corresponding amino acid sequence (SEQ ID NO: 2).

DETAILED DESCRIPTION OF THE INVENTION

In the course of these studies we surprisingly found, adjacent to a dihydrofolate reductase gene, an open reading frame (ORF) with the coding capacity for a 204 amino acid polypeptide with marked homology to mammalian IL-6 (P-value for homology searches with NCB/-BLAST: $P \leq 10\text{-}18$; percent identity/similarity to human IL-6: 24.74%/46.91%; to murine: 24.23%/47.94%; to porcine: 25.97%/52.91%; to bovine: 24.60%/49.73%; all alignments were calculated with the GCG software "GAP").

The viral gene product (v-IL-6) has conserved all 4 cysteine residues that are known to be involved in IL-6 disulfide bridging, and it shows a characteristic signal peptide of 19 to 22 amino acids (FIG. 1). The area involved in binding of human IL-6 to its receptor has been mapped to the middle of the protein by two groups[7,8,9]. Ehlers et al. showed that amino acids 105 to 123 of the human IL-6, as shown in FIG. 1 (GFNEEtCLVKlitGLLEFE)(residues 105-123 of SEQ ID NO:3), are involved in receptor binding. Most remarkably, this region is highly conserved in v-IL-6 (GFNEtsCLkKLadGFFEFE)(residues 87-105 of SEQ ID NO: 2). Identity and similarity of v-IL-6 to the receptor binding region of human IL-6 are 58% and 74%, respectively (FIG. 1). This is almost identical with the degree of conservation that can be observed in this receptor binding area of human IL-6 to murine IL-6. As both human IL-6 and murine IL-6 are able to bind to the receptor of the other species (murine IL-6 and human IL-6, respectively), it is likely that v-IL-6 is also able to bind to the human and the murine IL-6 receptor.

Rhadinoviruses frequently acquire genes from their host cell[10]. This HIV-8 ORF however, is the first known example of a viral IL-6 structural homologue. Up to now all cell-homologous genes of rhadinoviruses that have been tested were functional; non-functional genes would most likely have been lost in viral evolution. Thus, the conservation of essential IL-6 features makes it highly suggestive that v-IL-6 is functional in normal HHV-8 replication or persistence. Since models of paracrine growth stimulation of spindle cells by cytokines, including IL-6 and the related oncostatin M, have been proposed for KS pathogenesis, the finding of the v-IL-6 gene in HHV-8 lends support to the hypothesis that HHV-8 is causally related to this multifocal proliferation.

The present invention therefore relates to:

a) Viral interleukin-6 (v-IL-6), which can be obtained by recombinant expression of the DNA of HHV8.

b) A polypeptide, which can be obtained by recombinant expression of the DNA of HHV-8, and which comprises the amino acid sequence displayed in FIG. 2.

c) A fragment of v-IL-6, having the capability of binding to an IL-6 receptor and comprising the amino acid sequence GFNEtsCLkKLadGFFEFE (RESIDUES 87-105 of SEQ ID NO: 2).

d) A fragment as defined in b, which essentially comprises the amino acid sequence GFN EtsCLkKLadGFFEFE (residues of SEQ ID NO: 2).

e) A fragment as defined in c or d, which binds to a human IL-6 receptor.

f) A polypeptide having the amino acid sequence displayed in FIG. 2.

g) Mutants and variants of v-IL-6 or of the polypeptide, which can be obtained by recombinant expression of the DNA of HHV-8, and which comprises the amino acid sequence displayed in FIG. 2, which mutants and variants are obtained by conventional amino acid substitutions or deletions, with the proviso that these mutants and variants are functionally equivalent to v-IL-6.

h) Fragments of v-IL-6, or of the polypeptide, which can be obtained by recombinant expression of the DNA of HHV-8, and which comprises the amino acid sequence displayed in FIG. 2, characterized in that they are able to competitively inhibit the biological activity of IL-6 in a suitable assay system.

i) An isolated nucleic acid coding for v-IL-6 or the polypeptide, which can be obtained by recombinant expression of the DNA of HHV-8, and which comprises the amino acid sequence displayed in FIG. 2. A preferred embodiment is the nucleic acid having the nucleotide sequence of FIG. 2. Furthermore, an isolated nucleic acid, hybridizing to the above mentioned nucleic acids under stringent conditions and may comprise a sequence that encodes functionally active v-IL-6.

k) Monoclonal or polyclonal antibodies directed against v-IL-6 or the polypeptide, which can be obtained by recombinant expression of the DNA of HHV-8, and which comprises the amino acid sequence displayed in FIG. 2.

l) Testkit for the detection of v-IL-6 in a sample, comprising one or more of the above monoclonal or polyclonal antibodies.

m) Testkit for the detection of antibodies against v-IL-6 comprising v-IL-6 and/or the polypeptide, which can be obtained by recombinant expression of the DNA of HHV-8, and which comprises the amino acid sequence displayed in FIG. 2, and/or mutants and variants of v-IL-6 or the polypeptide, which can be obtained by recombinant expression of the DNA of HHV-8, and which comprises the amino acid sequence displayed in FIG. 2 and/or fragments of v-IL-6 or the polypeptide, which can be obtained by recombinant expression of the DNA of HHV-8, and which comprises the amino acid sequence displayed in FIG. 2.

n) Testkit for the detection of v-IL-6 DNA or RNA, comprising a nucleic acid which codes for v-IL-6, or which hybridizes to the aforementioned nucleic acid and encodes functionally active v-IL-6.

o) A medicament comprising as an active ingredient a monoclonal antibody or polyclonal antibodies directed against v-IL-6, or a polypeptide, which can be obtained by recombinant expression of the DNA of HHV-8, and which comprises the amino acid sequence displayed in FIG. 2, or mutants, variants or fragments of v-IL-6 or the aforementioned polypeptide. In another embodiment, the medicament may comprise as an active ingredient a nucleic acid encoding v-IL-6.

p) A cell culture growth medium, comprising as an active ingredient v-IL-6 or the polypeptide, which can be obtained by recombinant expression of the DNA of HHV-8, and which comprises the amino acid sequence displayed in FIG. 2, or mutants, variants or fragments of v-IL-6 or the aforementioned polypeptide.

q) A process of manufacturing v-IL-6 or the polypeptide, which can be obtained by recombinant expression of the DNA of HHV-8, and which comprises the amino acid sequence displayed in FIG. 2, or mutants and variants, or fragments of v-IL-6 or the aforementioned polypeptide.

r) A process of manufacturing a medicament, wherein the active ingredient is combined with suitable excipients and/or other auxiliary compounds according to common knowledge of those skilled in the art.

s) A process of manufacturing a medicament comprising as an active ingredient monoclonal or polyclonal antibodies directed against v-IL-6, or a polypeptide comprising v-IL-6, or mutants, variants or fragments of v-IL-6, or a nucleic acid encoding v-IL-6 for the treatment of kaposi sarcoma, Castleman's disease, multiple myeloma, kidney cell carcinoma, mesangial proliferative glomerulonephritis or B cell lymphoma.

t) A process of diagnosing an HHV-8 infection comprising the in vitro detection of v-IL-6 antigen, v-IL-6 DNA, v-IL-6 RNA or antibodies against v-IL-6.

u) A process of diagnosing the HHV-8 associated disorders kaposi sarcoma, Castleman's disease or body cavity based lymphomas (BCBL) through the diagnosis of an HHV-8 infection as described above.

v) A process of growing cells in culture, characterized in that v-IL-6 or the polypeptide, which can be obtained by recombinant expression of the DNA of HHV-8, and which comprises the amino acid sequence displayed in FIG. 2, or mutants and variants, or fragments of v-IL-6 or the aforementioned polypeptide, or mixtures of these compounds are contained in the growth medium. In a preferred process these cells are B-lymphocytes, hybridomas, hemopoietic cells or endothelial cells.

The sequence shown in FIG. 2 was generated by first subcloning shotgun fragments of lambda clone G16 into commercially available plasmid pBS KS-(Stratagene, San Diego, Calif.). Resulting plasmids were purified using a commercially available kit (Qiagen, Hilden, Germany) and sequenced on an automated sequencing system (A377, Applied Biosystems GmbH, Weiterstadt, Germany) using the recommendations of the manufacturer. The sequence was determined on both strands, using standard primers for shotgun clones, and gene specific primers for further analysis. In addition to showing the coding sequence of the interleukin-6 homologue of human herpesvirus 8, the deduced amino acid sequence, in one and three letter code, is shown in the sequence listing below.

The present invention is further described in the claims.

BIBLIOGRAPHY

1. Miles, S. A. et al.: *Science*, 255, 1432-1434 (1992).
2. Sturzl, M. et al.: Oncogene 10, 2007-2016 (1995).
3. Miles, S. A. et al.: Proc. Nat. Acad. Sci. U.S.A. 8 7, 4068-4072.
4. Masood, R. et al.: AIDS Res. Hum. Retroviruses 10: 969-975.
5. Chang, Y. et al.: Science. 266, 1865-1869 (1994).
6. Moore, P. S. et al.: J. Virol. 70, 549-558 (1996).
7. Hammacher, A. et al.: Protein Sci. 3, 2280-2293 (1994).
8. Ehlers, M. et al.: J. Immunol. 153, 1744-1753 (1994).
9. Ehlers, M. et al.: Ann. N.Y. Acad. Sci. 762, 400-402 (1995).
10. Albrecht, J. C. et al.: J. Virol. 66, 5047-5058 (1992).

The invention claimed is:

1. An isolated nucleic acid molecule comprising the sequence SEQ ID NO:1 and that encodes v-IL-6.

2. The isolated nucleic acid as described in claim 1, consisting of the nucleotide sequence of SEQ ID NO:1.

3. An isolated peptide having the amino acid sequence of SEQ ID NO:2 and obtained by recombinant expression of a DNA as described in claim 1 in an isolated cell.

4. An isolated nucleic acid molecule hybridizing under stringent conditions to the nucleic acid identical to SEQ ID NO:1 encoding functional v-IL-6.

5. A test kit for the detection of v-IL-6 DNA or RNA, comprising a nucleic acid molecule consisting of the sequence of SEQ ID NO:1 as claimed in claim 1.

6. A composition comprising as an active ingredient the nucleic acid as claimed in claim 1 and a pharmaceutically acceptable carrier.

* * * * *

SEQUENCE LISTING (1) GENERAL INFORMATION:

(iii) NUMBER OF SEQUENCES: 4

(2) INFORMATION FOR SEQ ID NO: 1:

(i) SEQUENCE CHARACTERISTICS:
    (A) LENGTH: 612 base pairs (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 1..612

(xi) SEQUENCE DESCRIPTION: SEQ ID NO: 1:

```
ATG TGC TGG TTC AAG TTG TGG TCT CTC TTG CTG GTC GGT TCA CTG CTG        48
Met Cys Trp Phe Lys Leu Trp Ser Leu Leu Leu Val Gly Ser Leu Leu
 1               5                  10                  15

GTA TCT GGA ACG CGG GGC AAG TTG CCG GAC GCC CCC GAG TTT GAA AAG        96
Val Ser Gly Thr Arg Gly Lys Leu Pro Asp Ala Pro Glu Phe Glu Lys
                20                  25                  30

GAT CTT CTC ATT CAG AGA CTC AAT TGG ATG CTA TGG GTG ATC GAT GAA       144
Asp Leu Leu Ile Gln Arg Leu Asn Trp Met Leu Trp Val Ile Asp Glu
         35                  40                  45

TGC TTC CGC GAC CTC TGT TAC CGT ACC GGC ATC TGC AAG GGT ATT CTA       192
Cys Phe Arg Asp Leu Cys Tyr Arg Thr Gly Ile Cys Lys Gly Ile Leu
 50                  55                  60

GAG CCC GCT GCT ATT TTT CAT CTG AAA CTA CCA GCC ATC AAC GAT ACT       240
Glu Pro Ala Ala Ile Phe His Leu Lys Leu Pro Ala Ile Asn Asp Thr
 65                  70                  75                  80

GAT CAC TGC GGG TTA ATA GGA TTT AAT GAG ACT AGC TGC CTT AAA AAG       288
Asp His Cys Gly Leu Ile Gly Phe Asn Glu Thr Ser Cys Leu Lys Lys
                 85                  90                  95

CTC GCC GAT GGC TTT TTT GAA TTC GAG GTG TTG TTT AAG TTT TTA ACG       336
Leu Ala Asp Gly Phe Phe Glu Phe Glu Val Leu Phe Lys Phe Leu Thr
            100                 105                 110

ACG GAG TTT GGA AAA TCA GTG ATA AAC GTG GAC GTC ATG GAG CTT CTG       384
Thr Glu Phe Gly Lys Ser Val Ile Asn Val Asp Val Met Glu Leu Leu
        115                 120                 125

ACG AAG ACC TTA GGA TGG GAC ATA CAG GAA GAG CTC AAT AAG CTG ACT       432
Thr Lys Thr Leu Gly Trp Asp Ile Gln Glu Glu Leu Asn Lys Leu Thr
130                 135                 140

AAG ACG CAC TAC AGT CCA CCC AAA TTT GAC CGC GGT CTA TTA GGG AGG       480
Lys Thr His Tyr Ser Pro Pro Lys Phe Asp Arg Gly Leu Leu Gly Arg
145                 150                 155                 160

CTT CAG GGA CTT AAG TAT TGG GTG AGA CAC TTT GCT TCG TTT TAT GTT       528
Leu Gln Gly Leu Lys Tyr Trp Val Arg His Phe Ala Ser Phe Tyr Val
                165                 170                 175

CTG AGT GCA ATG GAA AAG TTT GCA GGT CAA GCG GTG CGT GTT TTG GAC       576
Leu Ser Ala Met Glu Lys Phe Ala Gly Gln Ala Val Arg Val Leu Asp
            180                 185                 190

TCT ATC CCA GAC GTG ACT CCT GAC GTC CAC GAT AAG                       612
Ser Ile Pro Asp Val Thr Pro Asp Val His Asp Lys
        195                 200
```

(2) INFORMATION FOR SEQ ID NO: 2:

(i) SEQUENCE CHARACTERISTICS:
        (A) LENGTH: 204 amino acids
        (B) TYPE: amino acid
        (D) TOPOLOGY: linear (ii) MOLECULE TYPE: protein (xi) SEQUENCE DESCRIPTION: SEQ ID NO: 2:

```
Met Cys Trp Phe Lys Leu Trp Ser Leu Leu Leu Val Gly Ser Leu Leu
 1               5                  10                  15

Val Ser Gly Thr Arg Gly Lys Leu Pro Asp Ala Pro Glu Phe Glu Lys
```

-continued

```
                    20                  25                  30
Asp Leu Leu Ile Gln Arg Leu Asn Trp Met Leu Trp Val Ile Asp Glu
             35                  40                  45

Cys Phe Arg Asp Leu Cys Tyr Arg Thr Gly Ile Cys Lys Gly Ile Leu
         50                  55                  60

Glu Pro Ala Ala Ile Phe His Leu Lys Leu Pro Ala Ile Asn Asp Thr
 65                  70                  75                  80

Asp His Cys Gly Leu Ile Gly Phe Asn Glu Thr Ser Cys Leu Lys Lys
                 85                  90                  95

Leu Ala Asp Gly Phe Phe Glu Phe Glu Val Leu Phe Lys Phe Leu Thr
            100                 105                 110

Thr Glu Phe Gly Lys Ser Val Ile Asn Val Asp Val Met Glu Leu Leu
        115                 120                 125

Thr Lys Thr Leu Gly Trp Asp Ile Gln Glu Glu Leu Asn Lys Leu Thr
    130                 135                 140

Lys Thr His Tyr Ser Pro Pro Lys Phe Asp Arg Gly Leu Leu Gly Arg
145                 150                 155                 160

Leu Gln Gly Leu Lys Tyr Trp Val Arg His Phe Ala Ser Phe Tyr Val
                165                 170                 175

Leu Ser Ala Met Glu Lys Phe Ala Gly Gln Ala Val Arg Val Leu Asp
            180                 185                 190

Ser Ile Pro Asp Val Thr Pro Asp Val His Asp Lys
        195                 200
```

(2) INFORMATION FOR SEQ ID NO: 3:

(i) SEQUENCE CHARACTERISTICS:
        (A) LENGTH: 212 amino acids
        (B) TYPE: amino acid
        (C) STRANDEDNESS: <Unknown>
        (D) TOPOLOGY: linear (ii) MOLECULE TYPE: protein (xi) SEQUENCE DESCRIPTION: SEQ ID NO: 3:

```
Met Asn Ser Phe Ser Thr Ser Ala Phe Gly Pro Val Ala Phe Ser Leu
  1               5                  10                  15

Gly Leu Leu Leu Val Leu Pro Ala Ala Phe Pro Ala Pro Val Pro Pro
                 20                  25                  30

Gly Glu Asp Ser Lys Asp Val Ala Ala Pro His Arg Gln Pro Leu Thr
             35                  40                  45

Ser Ser Glu Arg Ile Asp Lys Gln Ile Arg Tyr Ile Leu Asp Gly Ile
         50                  55                  60

Ser Ala Leu Arg Lys Glu Thr Cys Asn Lys Ser Asn Met Cys Glu Ser
 65                  70                  75                  80

Ser Lys Glu Ala Leu Ala Glu Asn Asn Leu Asn Leu Pro Lys Met Ala
                 85                  90                  95

Glu Lys Asp Gly Cys Phe Gln Ser Gly Phe Asn Glu Glu Thr Cys Leu
            100                 105                 110

Val Lys Ile Ile Thr Gly Leu Leu Glu Phe Glu Val Tyr Leu Glu Tyr
        115                 120                 125

Leu Gln Asn Arg Phe Glu Ser Ser Glu Glu Gln Ala Arg Ala Val Gln
    130                 135                 140

Met Ser Thr Lys Val Leu Ile Gln Phe Leu Gln Lys Lys Ala Lys Asn
145                 150                 155                 160

Leu Asp Ala Ile Thr Thr Pro Asp Pro Thr Thr Asn Ala Ser Leu Leu
                165                 170                 175
```

-continued

```
Thr Lys Leu Gln Ala Gln Asn Gln Trp Leu Gln Asp Met Thr Thr His
            180                 185                 190

Leu Ile Leu Arg Ser Phe Lys Glu Phe Leu Gln Ser Ser Leu Arg Ala
            195                 200                 205

Leu Arg Gln Met
        210

(2) INFORMATION FOR SEQ ID NO: 4:

(i) SEQUENCE CHARACTERISTICS:
        (A) LENGTH: 211 amino acids
        (B) TYPE: amino acid
        (C) STRANDEDNESS: <Unknown>
        (D) TOPOLOGY: linear (ii) MOLECULE TYPE: protein (xi) SEQUENCE DESCRIPTION: SEQ ID NO: 4:

Met Lys Phe Leu Ser Ala Arg Asp Phe His Pro Val Ala Phe Leu Gly
  1              5                  10                 15

Leu Met Leu Val Thr Thr Thr Ala Phe Pro Thr Ser Gln Val Arg Arg
            20                  25                  30

Gly Asp Phe Thr Glu Asp Thr Thr Pro Asn Arg Pro Val Tyr Thr Thr
            35                  40                  45

Ser Gln Val Gly Gly Leu Ile Thr His Val Leu Trp Glu Ile Val Glu
        50                  55                  60

Met Arg Lys Glu Leu Cys Asn Gly Asn Ser Asp Cys Met Asn Asn Asp
 65                  70                  75                  80

Asp Ala Leu Ala Glu Asn Asn Leu Lys Leu Pro Glu Ile Gln Arg Asn
            85                  90                  95

Asp Gly Cys Tyr Gln Thr Gly Tyr Asn Gln Glu Ile Cys Leu Leu Lys
            100                 105                 110

Ile Ser Ser Gly Leu Leu Glu Tyr His Ser Tyr Leu Glu Tyr Met Lys
        115                 120                 125

Asn Asn Leu Lys Asp Asn Lys Lys Asp Lys Ala Arg Val Leu Gln Arg
130                 135                 140

Asp Thr Glu Thr Leu Ile His Ile Phe Asn Gln Glu Val Lys Asp Leu
145                 150                 155                 160

His Lys Ile Val Leu Pro Thr Pro Ile Ser Asn Ala Leu Leu Thr Asp
            165                 170                 175

Lys Leu Glu Ser Gln Lys Glu Trp Leu Arg Thr Lys Thr Ile Gln Phe
            180                 185                 190

Ile Leu Lys Ser Leu Glu Glu Phe Leu Lys Val Thr Leu Arg Ser Thr
            195                 200                 205

Arg Gln Thr
        210
```